(12) United States Patent
Jaffe

(10) Patent No.: US 12,109,227 B2
(45) Date of Patent: *Oct. 8, 2024

(54) COMPOSITION OF MATTER, SYSTEM, AND METHOD FOR ENHANCED MAGNESIUM UPTAKE, RETENTION, AND SYNERGISTIC ACTIONS

(71) Applicant: RMJH Holdings, LLC, Ashburn, VA (US)

(72) Inventor: Russell Jaffe, Vienna, VA (US)

(73) Assignee: RMJH Holdings, LLC, Ashburn, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/331,772

(22) Filed: Jun. 8, 2023

(65) Prior Publication Data

US 2024/0058376 A1 Feb. 22, 2024

Related U.S. Application Data

(63) Continuation of application No. 17/820,325, filed on Aug. 17, 2022, now Pat. No. 11,712,449.

(51) Int. Cl.
| | |
|---|---|
| *A61K 33/06* | (2006.01) |
| *A61K 9/48* | (2006.01) |
| *A61K 31/131* | (2006.01) |
| *A61K 31/194* | (2006.01) |
| *A61K 31/685* | (2006.01) |
| *A61P 9/12* | (2006.01) |

(52) U.S. Cl.
CPC ............ *A61K 33/06* (2013.01); *A61K 9/4825* (2013.01); *A61K 31/131* (2013.01); *A61K 31/194* (2013.01); *A61K 31/685* (2013.01); *A61P 9/12* (2018.01)

(58) Field of Classification Search
CPC ...... A61K 33/06; A61K 31/685; A61K 31/19; A61K 9/1075
See application file for complete search history.

(56) References Cited

U.S. PATENT DOCUMENTS

| | | | |
|---|---|---|---|
| 8,017,160 B2 * | 9/2011 | Jaffe ..................... | A61K 31/19 424/681 |
| 2005/0037998 A1* | 2/2005 | Jaffe ........................ | A61P 3/02 514/574 |
| 2007/0085059 A1* | 4/2007 | Mora-Gutierrez ........ | A61P 9/10 252/400.21 |
| 2013/0022673 A1* | 1/2013 | Jaffe .................... | A61K 31/685 424/682 |

OTHER PUBLICATIONS

Jaffe (Holistic Primary Care; The Alkaline Way:Ten Tips for Reversing Metabolic Acidosis, May 2015, vol. 1) (Year: 2015).*
Breznock et al (American Journal of Veterinary Research, 1978, vol. 39, pp. 977-980) (Year: 1978).*
Gavras (Hypertension, Abstract P109, Aug. 27, 2021) (Year: 2021).*
Moerkerke et al (Org. Biomol. Chem, 2017, vol. 15, pp. 8967-8974) (Year: 2017).*
H. Gavras, J. Neutel, R. Elin, A. Rosanoff, R. Costello, J. Mani, R. Jaffe. Abstract P109: A Promising Novel Hypertension Drug Candidate. Hypertension. 2021;78:AP109. Originally published Aug. 27, 2021https://doi-org.proxy.lib.duke.edu/10.1161/hyp.78.suppl_1.P109.
Schmitz, C., et al. (2004). "Dual-function ion channel/protein kinases: novel components of vertebrate magnesium regulatory mechanisms." Pediatr Res 55(5): 734-737.
Neustein S, Dimich I, Shiang H, et al. Cardiovascular consequences of the concomitant administration of nifedipine and magnesium sulfate in pigs. Int J Obstet Anesth 1998;7(4):247-50. http://www.ncbi.nlm.nih.gov/entrez/query.fcgi?cmd=Retrieve&db=PubMed&dopt=Citation&list_uids=15321188.
Nuoranne P. On the effect of food magnesium level on the activity of BASP, ALAT, ASAT and LD in pig serum. Nordisk veterinaermedicin 1978;30(2):74-82.http://www.ncbi.nlm.nih.gov/pubmed/634759.
Nuoranne PJ. On the effect of food magnesium level on serum magnesium, molar Mg:Ca and potassium value in pigs. Nordisk veterinaermedicin 1983;35(5-6):219-32. http://www.ncbi.nlm.nih.gov/pubmed/6889127.
Henrotte JG. [Erythrocyte magnesium and HLA groups]. C R Seances Acad Sci D 1979;289(4):445-7. http://www.ncbi.nlm.nih.gov/entrez/query.fcgi?cmd=Retrieve&db=PubMed&dopt=Citation&list_uids=117950.
Henrotte JG. The variability of human red blood cell magnesium level according to HLA groups. Tissue Antigens 1980;15(5):419-30.http://www.ncbi.nlm.nih.gov/entrez/query.fcgi?cmd=Retrieve&db=PubMed&dopt=Citation&list_uids=7444930.
Rosanoff, Andrea. "Magnesium supplements may enhance the effect of antihypertensive medications in stage 1 hypertensive subjects." Magnesium research 23, No. 1 (2010): 27-40.
Resnick, L. M., et al. (1990a). "RBC Cytosolic Free Calcium Levels in Hypertension: Relation to Blood Pressure and Other Cations." No. 1394. AJH 3(5): 59A.
Kuramoto T, Kuwamura M, Tokuda S, Izawa T, Nakane Y, Kitada K, Akao M, Guénet JL, Serikawa T. A mutation in the gene encoding mitochondrial $Mg^{2}+$ channel MRS2 results in demyelination in the rat. PLoS Genet. Jan. 6, 2011;7(1): e1001262. doi: 10.1371/journal.pgen.1001262. PMID: 21253565; PMCID: PMC3017111.
Schmitz C, Deason F, Perraud AL. Molecular components of vertebrate Mg2+-homeostasis regulation. Magnes Res. Mar. 2007;20(1):6-18. PMID: 17536484. https://www.jle.com/fr/revues/mrh/e-docs/molecular_components_of_vertebrate_mg_2_homeostasis_regulation_274006/article.phtml. Accessed Aug. 12, 2022.

(Continued)

Primary Examiner — Mark V Stevens
(74) Attorney, Agent, or Firm — ePatentManager.com; Guerry L. Grune

(57) ABSTRACT

The present disclosure relates to methods and complexes for ingestion of an elemental magnesium complex as inverted micellar nanodroplets designed to enhance uptake and cell delivery of active constituents. The complex and methods associated with delivery of the elemental magnesium complex disclosed improves many magnesium deficiencies that include cardiovascular, metabolic, neurohormonal, immune defense and repair systems, digestive, behavioral, and community risks.

2 Claims, No Drawings

(56) References Cited

OTHER PUBLICATIONS

Yamanaka R, Tabata S, Shindo Y, Hotta K, Suzuki K, Soga T, Oka K. Mitochondrial Mg(2+) homeostasis decides cellular energy metabolism and vulnerability to stress. Sci Rep. Jul. 26, 2016;6:30027. doi: 10.1038/srep30027. PMID: 27458051; PMCID: PMC4960558.
Phosal 35 SB. Material Specification Sheet. Phospholipid GmbH, Nattermannallee 1, D-50829 Cologne, Germany. Feb. 2007.

* cited by examiner

_US 12,109,227 B2_

COMPOSITION OF MATTER, SYSTEM, AND METHOD FOR ENHANCED MAGNESIUM UPTAKE, RETENTION, AND SYNERGISTIC ACTIONS

PRIORITY

This application is a continuation of and claims priority to U.S. application Ser. No. 17/820,325 filed Aug. 17, 2022, entitled "Composition of Matter, System, and Method for Enhanced Magnesium Uptake, Retention, and Synergistic Actions", the entirety of which are incorporated by reference herein.

TECHNICAL FIELD

The embodiments relate to the field of magnesium uptake, retention, and synergistic actions in cells and other physiologic fluids. Enhanced delivery systems accomplish better uptake and replenishment of magnesium in mammals. This results in multiple beneficial, synergistic effects.

BACKGROUND

This distinctive composition corrects deficits of exchangeable magnesium ($Mg^{++}$) throughout the body. Micellized soft gels containing inverted micellar nanodroplets that improve the uptake and retention of magnesium related functions in cells and systems that depend upon magnesium.

The usual calcium/magnesium ATPase ion channel saturates typically at one-third or less of the amount consumed. Thus, if the dose of magnesium salts consumed leads to retention of two-thirds the amount taken and this leads to hypermotility and then intestinal discomfort (typically diarrhea). Correct combinations of quaternary amines, mono-, di-, tri- or multi-carboxylic acids, and magnesium, as described, produce the novel results presented herein.

When measured in blood serum, low cell magnesium is associated with excess cell acids (cell metabolic acidosis). Impaired cell functions result. Magnesium deficiency links to impaired magnesium-dependent enzyme catalyst activation, impaired ATP activity, and impaired mitochondrial function due to loss of the proton gradient that depends upon intracellular magnesium. Thus, cell energy is impaired due to lack of receipt from the mitochondria of ATP. Chronic ill health and treatment resistance are often due to inadequate magnesium. Low cell magnesium is defined herein as being in the lower half of the serum magnesium range and is also known as chronic latent magnesium deficiency (CLMD).

Magnesium sufficiency is indicated by being in the upper half of the usual lab range for serum magnesium. Magnesium sufficiency includes a high intracellular Adenosine triphosphate (ATP) to Adenosine diphosphate (ADP) ratio, activation of magnesium dependent cell enzyme catalysts, reduced uptake of toxic minerals that are anti-nutrients, protection of essential fats in transit, along with maintenance of the cell proton gradient essential for mitochondrial cell battery functions.

There are many forms of magnesium. Soluble forms are generally preferred for replenishment of essential magnesium mineral.

Magnesium depletion is enhanced by distress, a mineral deficient diet, anti-nutrient pro-oxidative environmental toxins, and toxic minerals uptake especially when cell magnesium is low.

Existing magnesium wasting can be caused by thiazides and thiazide-like diuretics as well as other causes of magnesium wasting that counteract the antihypertensive effect of these diuretics and medications. This contributes to the lack of blood pressure control in too many patients treated with such medications.

We will be providing various evidence that micellized nanodroplet complexes of quaternary amines, magnesium, and appropriate counter ions greatly increases the magnesium uptake as determined by the independent serum and urine tests and other cardiovascular measures.

A combination of magnesium citrate micellized into stable nanodroplets with phosphatidylcholine increases magnesium absorption. This counteracts magnesium loss. This improves control of blood pressure and other physiologic functions performed by magnesium.

In this instance, wasting means the loss of magnesium in excess of what is required to maintain proper levels of the mineral in urine, sweat, and stool. Replenishment of tissue magnesium is elucidated below. Replenishment of tissue magnesium has previously been difficult because the calcium magnesium ATPase ion channel saturates at one third of the dose given.

The uniqueness here involves increasing the uptake of magnesium including a quaternary amine and counter ion to form micellized nanodroplets that are neutral in charge on the outside making them suitable for uptake by neutral pores that serve as uptake channels of nutrients, including minerals when combined as described herein. Neutral pores are the uptake channel(s) that accepts molecules that are neutrally charged on their exterior.

Definition of Terms

24°; in the medical community refers to a 24-hour period

Soft gel is a technique used to deliver some supplements and pharmaceuticals that is similar to the use of capsules, but the material of the outer shell is usually made of gelatin and the ingredients are almost always in liquid form.

SBP means either Systolic Blood Pressure or Seated Systolic Blood Pressure depending on the context.

DBP is seated diastolic blood pressure

MBP is seated median blood pressure which is (seated SBP+seated DBP)/2

ABPM is ambulatory blood pressure monitoring measurements.

PK is Pharmacokinetics

CRU is clinical research unit

CLMD is chronic latent magnesium deficiency

SUMMARY OF INVENTION

Our clinical work shows that a change in serum magnesium is correlated to improved vascular compliance, reduction in blood pressure in hypertensive individuals, and a concomitant increase in serum and urine magnesium levels. Pharmacokinetics from our clinical study suggests that a combination of magnesium citrate with phosphatidylcholine as nanodroplets increases magnesium absorption. In our clinical trial, uptake and retention of urine magnesium was about three-fold the maximum previously reported for uptake and retention of all other forms of magnesium salt delivery systems and was statistically significant.

Micellized delivery systems of enhanced magnesium appear to achieve uptake, retention, and functional benefits as described herein. The present disclosure relates to a composition of matter and system containing components including magnesium citrate and a quaternary amine that are micellized into stable nanodroplets.

The composition of matter may be formulated as an extended-release soft gelatin (soft-gel) capsule or otherwise. The present disclosure also relates to a method of administering a delivery system for enhanced magnesium uptake, retention, and functional benefits including administering extended release micellized soft gelatin (soft gel) capsules containing nanodroplets or controls.

Both the foregoing general description and the following description present embodiments intended to provide an overview or framework for understanding the nature and character of the disclosure.

DETAILED DESCRIPTION

The specific details of embodiments or variations described herein are to describe the composition and methods of use of the discovery. Any specific details of the embodiments are used for demonstration purposes only. They do not include limitations or all inferences to be understood from there.

The present disclosure describes composition of matter as stable delivery systems of enhanced magnesium uptake, retention, and their functional benefits as described herein. The present disclosure relates to a composition of matter including but not limited to, magnesium citrate also known as magnesium 2-hydroxypropane-1,2,3-tricarboxylate ($C_{12}H_{10}Mg_3O_{14}$), and a quaternary amine such as phosphatidylcholine or choline, and at least one carboxylic acid as counter ions such as citrate, malate, succinate, or other mono-, di-, or tri-carboxylic acids or functionally identical chemicals.

The present disclosure also relates to a method of administering a delivery system of enhanced magnesium in soft gelatin capsules containing, typically, the equivalent of 110 mg of elemental magnesium as inverted micellar nanodroplets in a dosing regimen of four capsules (440 mg), twice daily (880 mg supplement plus about 400 mg from diet per day).

Unprecedented uptake of magnesium can be accomplished by the novel interaction of the following components comprising magnesium, a quaternary amine, and a counter ion when ingested in the form of inverted micellized nanodroplets.

The invention will be better understood with reference to the following example in which the composition was administered in a single center, randomized, double-blind, placebo-controlled study that administered twice daily, four extended-release soft gelatin capsules each containing the equivalent of 110 mg of elemental magnesium or placebo.

Clinical Example

Phase I and II combined clinical trial tested the clinical tolerability, safety, and efficacy as well as the pharmacokinetics of 440 mg of the composition administered orally twice a day (total daily dose of 880 mg elemental magnesium) for 7 days compared to placebo in adult subjects with essential hypertension.

The following protocol was implemented. To screen subjects, if people were on other hypertension mediations than thiazide-like diuretics, these medications were removed prior to the study.

There was a subsequent washout period for three (3) days during which the blood pressure was monitored properly to determine if subject's blood pressure elevated to a dangerous level or not. This period was performed to ensure proper population selection.

SBP means either Systolic Blood Pressure or Seated Systolic Blood Pressure depending on the context.

The data disclosed includes seated systolic blood pressure (SBP), seated diastolic blood pressure (DBP), seated median blood pressure (MBP)=(seated SBP+seated DBP)/2] that will be correlated with other measures of cardiovascular performance. Not disclosed are any of the ambulatory blood pressure monitoring (ABPM) measurements. The Pharmacokinetics (PK) and Pharmacodynamics (PD) were measured to the extent possible given the short nature of the study (10 days).

Subjects that remained eligible after the run-in period were randomized using a 15:6 ratio to receive either 440 mg of the composition or placebo orally twice daily (i.e., total daily dose of 880 and 0 mg elemental magnesium, respectively) for a 7-day treatment period (Days 4-10). Subjects remained in the clinical research unit (CRU) on a low salt (2.5 g/24 hours) diet containing about 400 mg elemental magnesium for the run-in period through the 24-hour post treatment assessments (Day 11) and throughout the study. Subjects returned to the clinic 8 days (±3 days) after the last dose of the active composition or placebo for their final study visit.

The 21 subjects (n=21) in the trial were randomized in a 15:6 ratio to the composition or placebo. The actual number of subjects eligible for randomization at the end of the run-in period in the cohort exceeded the projection by 1, and all eligible subjects were randomized to treatment. Thus, the total number randomized was 22 rather than the planned 21.

The actual number of subjects randomized and analyzed are shown in Table 1 as follows:

TABLE 1

| Number of Subjects for Initial Clinical Trial | | | |
|---|---|---|---|
| | Composition | Placebo | Total |
| Randomized population | 16 | 6 | 22 |
| Safety population | 16 | 6 | 22 |
| Pharmacokinetic (PK) population | 16 | 6 | 22 |
| Efficacy population (the number of patients who completed the study not the total that began) | 15 | 6 | 21 |

Subjects had to be 18-80 years old people with essential hypertension that was either recently diagnosed (for which the subject had not yet started taking anti-hypertensive medications) or previously diagnosed (for which the subjects were taken off all anti-hypertensive therapy to participate in the study or for which the subject had been off treatment for >1 week before starting the study). To be randomized to treatment, subjects had to have pre-dose Day 4 SBP≥150 and ≤200 mmHg and DBP≥95 and ≤115 mmHg after resting for 5 minutes in the seated position.

This randomized to treatment procedure as well as measurements and assessments made were based upon the definitions provided by the American Heart Association, the American College of Cardiology and the National Heart Lung and Blood Institute (NIH).

One subject was withdrawn from the study on Day 9. She received her last dose of the composition treatment on Day 7 of the study. Her vital signs and blood pressure were monitored on Days 8 and 9 of the study, and SBP as well as ABPM data was collected but only the SBP was disclosed from Day 8 to Day 9. Her PK data was included in the retrospective PK analyses for Days 4-8 (and not Days 9-11, as data for these later times was not available). The reason for the protocol exclusion was because her systolic blood pressure dropped below 110 (to 108 from 155) and might have indicated hypotension, but it did not. She was carefully monitored for hypotension which she did not have. The Data Safety Management Board did not consider this a reportable adverse event.

Examination of the data confirms that for blood pressure measurements, ABPM correlates tightly with properly done seated blood pressure (SBP) measurements.

Subjects that remained eligible were taken off their non-thiazide anti-hypertensive medications (if any) and underwent a 7-day washout period. Subjects that remained eligible after the washout period and subjects that did not require a washout (recently diagnosed or previously diagnosed and off treatment for >1 week before starting the study) received placebo orally twice daily for a 3-day run-in period (Days 1-3).

To evaluate the changes over the study time from baseline (Day 3 to pre-dose Day 4) in mean daytime, systolic and diastolic (8 AM to 4 PM) ABPM SBP, MBP and DBP ($SBP_{day}$, $MBP_{day}$, and $DBP_{day}$, respectively) after 7 days of treatment (Day 10 to Day 11) with the composition compared to placebo in adult subjects with essential hypertension.

To evaluate the changes from baseline (Day 3 to pre-dose Day 4) in mean nighttime (10 PM to 6 AM) systolic and diastolic (10 PM to 6 AM) ABPM. SBP and DBP ($SBP_{night}$ $MBP_{night}$, and $DBP_{night}$, respectively) after 7 days of treatment (Day 10 to Day 11) with the composition compared to placebo in adult subjects with essential hypertension. We evaluated the change from baseline (Day 3 to pre-dose Day 4) in mean 24-hour ABPM, SBP and DBP ($SBP_{24\ hr}$ and $DBP_{24\ hr}$, respectively) after 7 days of treatment (Day 10 to Day 11) with the composition compared to placebo in adult subjects with essential hypertension. This was to evaluate the change from baseline (pre-dose Day 4) in SBP and DBP after 7 days of treatment (Day 11) with the composition compared to placebo in adult subjects with essential hypertension.

The protocol-specified efficacy analyses were based on all randomized subjects who completed 7 days of the active composition or placebo, as well as the Day 4 (pre-dose) and Day 11 SBP and DBP assessments or the Day 3 to Day 4 (pre-dose) and Day 10 to Day 11 ABPM assessments.

The composition was administered as soft gelatin capsules. The ingredients included medium-chain triglycerides [National Formulary (NF)], Phosal® 35 SB, gelatin (NF), vegetable derived glycerol, 99.7% [United States Pharmacopeia (USP)], titanium dioxide (USP) an opacifying agent, and purified water (USP). The Phosal® 35 SB contains 34-53% lecithin containing ≥91% phosphatidylcholines, soya, 10-25% sunflower oil, 5-10% soya fatty acids, or other sources of quaternary amines, and 0.1-1% DL α-tocopherol. A single strength 110 mg elemental magnesium/capsule was used for this example wherein the 110 mg elemental magnesium is provided as inverted micellar nanodroplets.

Soft gelatin capsules that were visually indistinguishable from the active oral dosage form were used as placebo. The placebo contained the same inactive ingredients as the active, with the exception that mannitol powder, USP, in place of Phosal 35 SB was added to allow for a placebo according to the observer clinicians and pharmacists who did the study randomization that shows comparability between active and placebo to the study participants in the absence of active ingredients in the placebo.

During the run-in period, subjects took 4 placebo capsules orally twice daily at 8 AM (±60 minutes) and 8 PM (±60 minutes) for 3 days (Days 1-3).

During the treatment period, subjects were randomized in a ratio of 16:6 to receive either 4 capsules of the composition (440 mg elemental magnesium) or 4 capsules of placebo orally both twice daily at 8 AM (±60 minutes) and 8 PM (±60 minutes) [i.e., total daily dose of 880 and 0 mg elemental magnesium, respectively] for 7 days (Days 4-10). All doses were taken in the CRU.

Data from all randomized subjects who completed 7 days of the active composition or placebo treatment, as well as the Day 3 to pre-dose Day 4 and Day 10 to Day 11 ABPM assessments or the Day 4 (pre-dose) and Day 11 SBP and DBP assessments were included in the efficacy analyses for changes in mean daytime, nighttime, and 24-hour ABPM and SBP and DBP, respectively.

Individual ABPM $SBP_{day}$, $SBP_{night}$, $SBP_{24\ hr}$, $DBP_{day}$, $DBP_{night}$, and $DBP_{24\ hr}$ were listed for all randomized subjects. The listings include calculations of change from baseline for the post-dose interval (i.e., Day 10 to Day 11). The pre-dose interval (Day 3 to Day 4) served as the baseline for these calculations. Individual $SBP_{day}$, $SBP_{night}$, $SBP_{24\ hr}$, $DBP_{day}$, $DBP_{night}$, and $DBP_{\geq h}$ were summarized descriptively by treatment group for the efficacy population.

Mean, median, minimum, maximum, and their standard deviation (SD) were used to summarize the data, and the data are presented in tabular format. Descriptive statistics for the individual changes in ABPM measurements from baseline (Day 3 to pre-dose Day 4) to the post-dose assessment (Day 10 to Day 11) are included.

Individual SBP and DBP (all seated) values are summarized descriptively by treatment group for the efficacy and controls populations. Again mean, median, minimum, maximum, and SD were used to summarize the data. Descriptive statistics for individual changes in SBP and DBP measurements as well as ABPM from baseline (pre-dose Day 4) to each assessment after the first randomized dose of the active composition or placebo were included.

Efficacy Results

Following the 7-day washout/run-in period (for subjects taking antihypertensives) and 2 days of run-in placebo period where the subjects remained in the CRU on a low salt (2.5 g sodium/24 hours) diet, the baseline (Day 3 to pre-dose Day 4) mean±SD $SBP_{day}$ was 147.4±9.6 mmHg for the placebo group and 150.4±13.5 mmHg for the study group. Thus, the mean $SBP_{day}$ for the composition treatment group was slightly higher than for the placebo group (difference of 3 mmHg) before administration of the first randomized dose of the active composition or placebo.

At the end of treatment (Day 10 to Day 11), the mean±SD $SBP_{day}$ was 149.0±11.0 mmHg in the placebo group and 145.8±17.7 mmHg in the study group. The corresponding mean±SD changes from baseline were 1.6±11.4 mmHg in the placebo group and −4.6±11.7 mmHg in the study group. The increase of 1.6 mmHg in the placebo group and decrease of 4.6 mmHg in the study group results in a total difference of 6.2 mmHg between treatment groups with regards to change from baseline. The baseline mean±SD $DBP_{day}$ was 93.3±9.8 mmHg for the placebo group and 92.8±11.6 mmHg for the study group. Thus, the mean $DBP_{day}$ values of the placebo and the study groups were comparable before administration of the first randomized dose of the active composition or placebo.

At the end of treatment, the mean±SD $DBP_{day}$ was 92.1±12.3 mmHg in the placebo group and 89.4±10.7 mmHg in the study group. The corresponding mean±SD changes from baseline were −1.2±17.1 mmHg in the placebo group and −3.5±6.9 mmHg in the study group. The decrease of 1.2 mmHg in the placebo group and a decrease of 3.5 mmHg in the study group resulted in a total difference of 2.3 mmHg between treatment groups with regard to changes in ABPM from baseline.

The baseline mean for ABPM $SBP_{night}$±SD was 133.3±9.3 mmHg for the placebo group and 139.2±17.2 mmHg for the study group. Thus, the mean $SBP_{night}$ for the composition treatment group was slightly higher than for the placebo group (difference of 5.9 mmHg) before administration of the first randomized dose of the active composition or placebo.

At the end of treatment for ABPM, the mean±SD $SBP_{night}$ was 134.0±10.1 mmHg in the placebo group and 135.0±15.5 mmHg in the study group. The corresponding mean±SD changes from baseline were 0.7±12.1 mmHg in the placebo group and −4.2±12.5 mmHg in the study group. The increase of 0.7 mmHg in the placebo group and decrease of 4.2 mmHg in the study group results in a total difference of 4.9 mmHg between treatment groups with regards to change from baseline.

The baseline mean±SD ABPM $DBP_{night}$ was 82.6±3.2 mmHg for the placebo group and 82.9±12.3 mmHg for the study group. Thus, the mean $DBP_{night}$ values of the placebo and the study groups were comparable before administration of the first randomized dose of the active composition or placebo.

At the end of treatment for ABPM, the mean±SD $DBP_{night}$ was 82.0±9.6 mmHg in the placebo group and 81.0±10.4 mmHg in the study group. The corresponding mean±SD changes from baseline were −0.6±7.5 mmHg in the placebo group and −1.9±8.8 mmHg in the study group. The decrease of 0.6 mmHg in the placebo group and decrease of 1.9 mmHg in the study group results in a total difference of 1.3 mmHg between treatment groups with regards to change from baseline.

The baseline mean±SD for ABPM was $SBP_{24\,h}$, was 141.2±8.1 mmHg for the placebo group and 146.2±14.1 mmHg for the study group. Thus, the mean ABPM $SBP_{24\,h}$, for the composition treatment group was slightly higher than for the placebo group (difference of 5.0 mmHg) before administration of the first randomized dose of the active composition or placebo.

At the end of treatment, the mean±SD ABPM $SBP_{24\,hr}$ was 143.5±10.0 mmHg in the placebo group and 142.4±16.0 mmHg in the study group. The corresponding mean±SD changes from baseline were 2.3±11.6 mmHg in the placebo group and −3.8±11.7 mmHg in the study group. The increase of 2.3 mmHg in the placebo group and decrease of 3.8 mmHg in the study group results in a total difference of 6.1 mmHg between treatment groups with regards to change from baseline.

The baseline mean±SD ABPM DBP 24 hr was 88.8±6.0 mmHg for the placebo group and 89.1±11.1 mmHg for the study group. Thus, the mean $DBP_{\geq h}$, values of the placebo and the study groups were comparable before administration of the first randomized dose of the active composition or placebo.

At the end of treatment, the mean±SD ABPM DBP 24 hr was 89.1±11.3 mmHg in the placebo group and 86.9±10.1 mmHg in the study group. The corresponding mean±SD changes from baseline were 0.3±6.5 mmHg in the placebo group and −2.3±7.0 mmHg in the study group. The increase of 0.3 mmHg in the placebo group and decrease of 2.3 mmHg in the study group results in a total difference of 2.6 mmHg between treatment groups with regards to change from baseline.

At the end of treatment (Day 11), the mean±SD SBP was 154.8±5.6 mmHg in the placebo group and 146.1±15.4 mmHg in the study group. The corresponding mean±SD changes from baseline were −7.2±7.4 mmHg in the placebo group and −14.6±13.6 mmHg in the study group. The decrease of 7.2 mmHg in the placebo group and decrease of 14.6 mmHg in the study group results in a total difference of 7.4 mmHg between treatment groups with regards to changes from baseline.

The baseline mean±SD DBP was 102.0±5.2 mmHg for the placebo group and 101.1±5.2 mmHg for the study group. Thus, the mean DBP values for the placebo and the study groups were comparable before administration of the first randomized dose of the active composition or placebo.

At the end of treatment, the mean±SD DBP was 99.7±10.8 mmHg in the placebo group and 94.7±7.4 mmHg in the study group. The corresponding mean±SD changes from baseline were −2.3±6.3 mmHg in the placebo group and −6.4±6.1 mmHg in the study group. The decrease of 2.3 mmHg in the placebo group and decrease of 6.4 mmHg in the study group results in a total difference of 4.1 mmHg between treatment groups with regards to change from baseline.

The baseline mean±SD MBP was 132.0±3.4 mmHg for the placebo group and 130.9±6.0 mmHg for the study group. Thus, the baseline MPB values for the placebo and the study groups were comparable to what was seen for SBP and DBP analyzed individually.

At the end of treatment, the mean±SD MBP was 127.3±7.6 mmHg in the placebo group and 120.4±10.2 mmHg in the study group. The corresponding mean±SD changes from baseline were −4.8±6.1 mmHg in the placebo group and −10.5±8.7 mmHg in the study group. The decrease of 4.8 mmHg in the placebo group and decrease of 10.5 mmHg in the study group results in a total difference of 5.7 mmHg between treatment groups with regards to changes from baseline. Thus, the end of treatment total difference in MBP between treatment groups (5.7 mmHg) fell between the end of treatment total differences for the individually analyzed parameters (7.4 mmHg for SBP and 4.1 mmHg for DBP).

No statistically significant correlations were observed but favorable trends were between individual changes in observed total serum magnesium $AUC_{0-24}$ and ABPM ($SBP_{day}$, $SBP_{night}$, and $SBP_{24\,hr}$) from baseline to end of treatment. Weak correlations were noted between individual changes in observed 24-hour urinary magnesium excretion and ABPMs ($SBP_{day}$, $SBP_{night}$, and $SBP_{24\,hr}$) from baseline to end of treatment. The correlation of decreasing ABPM with increasing observed 24° urinary magnesium excretion was more pronounced for the daytime ABPM than the nighttime ABPM.

Statistically significant correlations were observed between individual changes in observed total serum magnesium $AUC_{0-24}$ and ABPM ($DBP_{day}$, $DBP_{night}$, and DBP 24 hr) from baseline to end of treatment. The same was true for the comparisons of 24° urinary magnesium excretion and ABPM measures.

There were significant correlations for individuals between changes in observed total serum magnesium concentration correlated with seated blood pressures and ABPM (SBP, DBP, and MBP) from baseline to end of treatment. Comparisons of 24° urinary magnesium excretion and seated blood pressure and ABMP for the group studied were found to be statistically significant.

The meaningful trends regarding the observations made for the serum magnesium concentration deserve more study. As part of a retrospective analysis, if the study N had been 100, rather than the 21 studied, the study would have reached p=<0.05 significance for changes in serum as well as urine magnesium correlated to systolic and diastolic blood pressure change.

There is a correlation known as CLMD, which is chronic latent magnesium deficiency. This means that if a subject is in the lower half of the serum magnesium range their blood pressure will be higher and their cardiovascular performance will be worse. This also means that if the subject is in the upper half of the serum magnesium range, they will have lower blood pressure and better cardiovascular performance.

This also means that because magnesium is water soluble it is regulated by the kidneys, perspiration, and stool and therefore cannot go above the upper value for the lab range.

If a subject is below the lower limit of the range for serum magnesium they have hypomagnesemia, a more severe and profound magnesium deficiency.

The details of the clinical study follow.

After 7 days of treatment with the composition in adult subjects with essential hypertension, the ABPM decreased from baseline for all ABPM parameters (mean change: −4.6, −3.5, −4.2, −1.9, −3.8, and −2.3 mmHg for $SBP_{day}$, $DBP_{day}$, $SBP_{night}$, $DBP_{night}$, $SBP_{24\ hr}$, and $DBP_{24\ hr}$, respectively). The ABPM in the placebo group either decreased to a lesser extent or increased, resulting in total differences in mean change from baseline between treatment groups of 6.2, 2.3, 4.9, 1.3, 6.1, and 2.6 mmHg, respectively. The decreases were more pronounced during the day than at night.

Consistent with the ABPM findings, the seated blood pressures in the study group decreased from baseline to end of treatment for both SBP and DBP (mean change of −14.6 and −6.4 mmHg, respectively). The seated blood pressures in the placebo group decreased to a lesser extent, resulting in total differences in mean change from baseline between treatment groups of 7.4 and 4.1 mmHg, respectively. The exploratory analysis of change from baseline to end of treatment in a combined version of the two seated blood pressure parameters [i.e., MBP=(seated SBP+seated DBP)/2] was also consistent with the ABPM results, and the total difference in MPB between treatment groups (5.7 mmHg) fell between that detected for the individually analyzed parameters and the treatment groups.

Reanalysis of the ABPM and seated blood pressure during the day showed tight correlation for the efficacy endpoints for the safety population. One subject achieved such blood pressure reduction after 5 days that they were removed from protocol despite no adverse event such as hypotension occurred. The decreases in blood pressure were greater for all parameters, as were the total differences in mean change from baseline between treatment groups (7, 2.6, 5.2, 1.9, 6.6, 2.8, 9.4, and 5.6 mmHg for ABPM $SBP_{day}$, $DBP_{day}$, $SBP_{night}$, $DBP_{night}$, $SBP_{24\ hr}$, DBP 24 hr, overall SBP, and overall DBP, respectively).

This reduction in blood pressure over a such a short treatment period (7 days) would be what would be expected over 12 weeks for patients undergoing thiazide diuretic treatments. This demonstrates a useful potential treatment for essential hypertension and potential for cardiovascular, metabolic, and other molecular therapies dependent upon magnesium replenishment. This enhanced uptake was measured in urine as well as serum and was accomplished by the unique interaction of components comprising magnesium, a quaternary amine, and a counter ion when ingested as inverted micellar nanodroplets.

Pharmacokinetic Results

The mean±SD observed total serum magnesium—the area under the curve ($AUC_{0-24}$) values—at baseline (Day 3) were comparable for the placebo and the study groups (42.8±2.8 mEq*24 hr/L and 41.4±2.4 mEq*24 hr/L, respectively).

The mean observed total serum magnesium $AUC_{0-24}$ values after 1 and 7 days of randomized placebo treatment did not substantially change from baseline, with decreases of 1.01-fold (Day 4) and 1.03-fold (Day 10), respectively. Increases (1.06-fold) in mean observed total serum magnesium $AUC_{0-24}$ from baseline were noted after 1 and 7 days of the composition treatment (43.9±2.5 and 43.9±1.9 mEq*24 hr/L, respectively).

The mean±SD observed total serum magnesium values at baseline (within one hour before the first randomized dose on Day 4) were comparable for the placebo and the study groups (1.78±0.117 and 1.75±0.103 mEq/L, respectively).

The mean±SD ratios of observed total serum magnesium trough concentrations at Days 5-10 (i.e., within one hour before each morning the active composition or placebo dose) relative to baseline did not substantially change for the placebo group (mean ratios ranged from 0.96 to 1.02). Increases in the mean ratios of observed total serum magnesium concentrations relative to baseline were noted in the study group, starting at Day 5 (1.09±0.06), peaking at Day 6 (1.10±0.07), and returning to no substantial change by Day 10 (1.02±0.08). More precise analyses may be needed to distinguish meaningful differences.

This trend of increases in observed total serum magnesium levels early during the 7-day treatment period and return to levels comparable to baseline by the end of treatment period in the study group with no substantial change in the placebo group was also apparent in the plots of individual total serum magnesium concentration data over time. This includes both for the observed and corrected values. If 100 people had been studied, retrospective analysis of the data (serum magnesium change) would correlate to blood pressure change.

The mean±SD ABPM observed 24-hour urinary magnesium excretion values at baseline (Day 3) were comparable for the placebo and the study groups (7.0±4.3 mEq/24 hr and 7.3±2.6 mEq/24 hr, respectively).

The mean observed 24-hour urinary magnesium excretion after 1 and 7 days of randomized placebo treatment did not substantially change from baseline, with decreases of 1.2-fold at both Days 4 and 10. In contrast, increases of 1.3-fold and 2.3-fold in mean observed 24-hour urinary magnesium excretion from baseline were noted after 1 and 7 days of the composition treatment (9.8±3.9 and 16.5±6.2 mEq/24 hr, respectively) and were significant.

The mean corrected 24-hour urinary magnesium excretion after 1 and 7 days of randomized placebo treatment were comparable. In contrast, the mean corrected 24-hour urinary magnesium excretion increased by 3.5-fold after 7 days of the composition treatment relative to 1 day of the composition treatment (9.1±5.4 and 2.6±3.0 mEq/24 hr, respectively). Thus, the increase in 24-hour urinary magnesium excretion was more pronounced for the corrected levels (i.e., with the endogenous urinary magnesium excretion subtracted) than the observed levels.

This increasing 24-hour urinary magnesium excretion over the course of the 7-day treatment period in the study group with no substantial change in the placebo group was significant at p=<0.05 level and was also significant in individual 24-hour urinary magnesium excretion data over time, including both for the observed and corrected values.

Pharmacokinetic Conclusions

Increases from baseline in mean values observed total serum magnesium $AUC_{0-24}$ (without correction for endogenous magnesium levels) were noted after 1 and 7 days of the composition treatment (1.1-fold for both). Further, increases from baseline in mean observed total serum magnesium through levels on Days 5-10 (within one hour before each morning the active composition or placebo dose was administered) were observed for the composition, starting at Day 5 (1.1-fold), peaking at Day 6 (1.1-fold), and returning to no substantial change by Day 10 (1.0-fold).

Substantial increases from baseline in mean ABPM values observed for 24-hour urinary magnesium excretion were noted after 1 and 7 days of the composition treatment (1.3 and 2.3-fold, respectively). This increase was more pronounced for the mean corrected 24-hour urinary magnesium excretion, where the endogenous urinary magnesium excretion was subtracted (increase of 3.5-fold after 7 days of treatment relative to 1 day of treatment). The relatively large increases in observed 24-hour urinary magnesium excretion coupled together with the slight increases in observed total serum magnesium are indicative of unprecedented uptake of elemental magnesium and its displacement of metabolic acids into the urine. This may be accomplished by the unique interaction of components comprising magnesium, a quaternary amine, and a counterion when ingested in the form of inverted micellar nanodroplets consistent with the known tight regulation of exchangeable magnesium in the body (magnesium homeostasis).

These exploratory analyses evaluate relationships between the changes in magnesium levels and the changes in blood pressure suggesting that changes in observed 24-hour urinary magnesium excretion may be the better indicator of the efficacy of the drug candidate.

The composition (compared with total serum magnesium $AUC_{0-24}$) was sufficient for the short-term trials (7 days of dosing). Longer trials need to be performed to more specifically determine the exact relationship between blood pressure, serum magnesium and urine magnesium.

More specifically, the enhancement of serum magnesium as it correlates to urine pH after rest was studied separately. This included administering proper oral magnesium plus choline citrate doses to over 5000 people after they had experienced a minimum of 6 hours of rest. The determination was made to determine the proper dosage based on urine pH testing. Healthier range was 6.5-7.5 and indicated that 2 doses per day of 220 mg of elemental magnesium plus one concurrent teaspoon of choline citrate containing a total of 1300 mg of choline citrate would maintain their exchangeable magnesium level. For urine pH below 6.5, a single additional dose of magnesium plus choline citrate should be administered for each half (0.5) urine pH unit below 6.5. The study revealed that the intake of the magnesium plus choline citrate supplement was directly related to the urine pH after rest presumably because the formulation appeared to form stable neutrally charged on the outside nanodroplets. It was also discovered that cell magnesium/cell metabolic acidosis correlated with the urine pH after rest data.

Modulation by bioavailable magnesium has additional positive effects on essential fats and endocannabinoids. Endocannabinoid receptors exist in higher concentrations within the brain and the intestinal "gut" nervous system than anywhere else in the body. With enough activated calcium and bioavailable magnesium present in the system, the gut-brain axis is satiated, and a state of poise and relaxation is achieved.

The magnesium/calcium balance is the second messenger for hormones (a known biological phenomenon) which translates into providing the activity pathway hormones will follow. In our experience, most subjects were found to exhibit higher than needed calcium levels and lower than desired magnesium levels so that essential fat protection from oxidation was insufficient as was the ability to maintain endocannabinoid receptors from being too excited. The proper level of magnesium also protects from metabolic acidosis that occurs when the cell magnesium is low—again found to be endemic in the general population today.

More specifically, the modulation of magnesium which exchangeable and therefore is biologically active and biologically active.

CLMD occurs in many studied populations. Each lab sets its own range. Being in the lower half of the lab usual range for magnesium qualifies as CLMD. Being in the upper half of the serum range for magnesium qualifies as magnesium sufficient and the subject does not have CLMD. Those subjects with serum magnesium levels below the lower half exhibit hypomagnesia rather than CLMD.

Our studies have also allowed us to confirm in the real world that the morning urine pH assesses how many doses of magnesium plus choline citrate are needed throughout the day.

The discussion above, regarding proper modulation of bioavailable or exchangeable magnesium can help reduce the risk factors for strokes, vasculitis, and other circulatory health issues.

All the examples of physiologic functions below are known to be made worse by low serum or urine magnesium and to be made better by magnesium replenishment in serum and urine. Examples of items that directly affect Mg levels in the general world population(s) include anti-nutrient pro-oxidative chemicals. There are five (5) categories of such anti-nutrients which are pro-oxidative—which means they consume essential antioxidants.

These are listed below as:
(i) Persisting organic pollutants: POPs such as PFAS, DDT, DDE, PCBs, heptachlor, kepone and other similar hormone disrupters
(ii) Solvent residues: VOCs such as TCE, methylene chloride, toluene, ortho-toluene, benzene, and xylene
(iii) Toxic metals: examples include lead, mercury, arsenic, cadmium, and nickel
(iv) Mold products: products produced by molds including spores, harmful chemicals, and other products of fungal proliferation
(v) Radioisotopes: Radon and other radioisotopes either naturally occurring or manmade The following description of variants is only illustrative of components, elements, acts, products, and methods considered to be within the scope of the invention and are not in any way intended to limit such scope by what is specifically disclosed or not expressly set forth. The components, elements, acts, products, and methods as described herein may be combined and rearranged other than as expressly described herein and the present disclosures are included.

Variations in composition are examples of what the synergistic nanodroplet complex accomplishes. The exterior of the nanodroplet is neither positively charged nor negatively charged so that the outer shell remains neutrally charged while the inner portion of the nanodroplet has balanced charged populations.

The present disclosure includes at least the following variations and/or embodiments that represent that already described above.

More specifically, the present disclosure provides for a magnesium complex comprising magnesium citrate; and a quaternary amine.

Here the magnesium complex includes magnesium citrate that is chemically named magnesium 2-hydroxypropane-1,2,3-tricarboxylate.

In addition, the quaternary amine comprises phosphatidylcholine and/or choline. The complex includes at least one mono- di-, or tri-carboxylic acid. Typically, the complex comprises one or more of a group consisting of citrate, malate, succinate, and fumarate or similar counter ion.

Also, the magnesium complex forms a combination with choline and/or phosphatidylcholine wherein said quaternary amine must include an appropriate class of counter ions where the counter ions include all possible choline counter ions including but not limited to one or more of choline citrate, choline malate, choline fumarate, choline succinate, choline glycinate, choline ascorbate, choline taurate, choline pidolate, choline bitartrate, choline bis-salicylate and all lecithins that contain phosphatidylcholine or its derivatives.

In a further embodiment the magnesium complex together with said quaternary amine provides nanodroplets that are neutrally charged on an exterior surface of the nanodroplets and wherein within the nanodroplets there exists equal amounts of both negative and positive charges. Within the nanodroplets there exists magnesium plus choline and/or phosphatidylcholine or other quaternary amines plus a functionally suitable counter ion.

The magnesium complex includes compositions of nanodroplets that function to enhance the uptake and functional retention of exchangeable magnesium and as a result and reduce gastrointestinal distress in adults.

In yet another embodiment, the magnesium complex comprises 110 mg of elemental magnesium and the magnesium complex is provided in a micellized soft-gel capsule wherein each capsule contains 110 mg of elemental magnesium as nanodroplets.

Here, the magnesium containing soft-gel is formulated and provided as inverted micellar nanodroplets wherein the inverted micellar nanodroplets are neutral on the outside while containing balanced charges on the inside.

It is understood that the magnesium citrate and the quaternary amine can be combined wherein the magnesium citrate and the quaternary amine can be combined in an aqueous and/or solid combination.

It is also possible that the magnesium citrate and the quaternary amine can be combined into a form of a tablet.

The magnesium complex further comprises at least one alkalinizing acid such as a Krebs salt.

The magnesium complex has been formulated when consumed in appropriate doses to reduce one or more of a group of mammalian conditions and/or symptoms when compared with not consuming the appropriate doses of the complex:
long digestive transit time;
atrial fibrillation;
restless leg syndrome;
Barlow's mitral valve prolapse;
deep vein thrombosis (DVT);
endocarditis;
immune complex vasculitis;
autoimmune disease;
infectious chronic disease;
heart arrythmias;
chronic kidney disease;
liver disease;
eczema and psoriasis;
skin hyperproliferation;
immune impairment;
autoimmune compromised mammalian systems;
chronic fatigue;
repair deficiency;
impaired cell protein synthesis;
cell proton gradient mitochondrial functions;
improvement in SF-36 symptom score;
improvement in cell electron flow;
improvement in neurochemical balance including measurement of an adrenaline/serotonin ratio;
improvement in cell protective buffering gradient capacities;
improvement in restorative sleep;
reduction in depression and mood disorders;
improvement in overall productivity and performance of mammalian systems;
improvement in physical and mental endurance measured by number and complexity of tasks performed;
improvement in cell energetic performance as measured by quantifying individual or collective cell energy including measurement of ATP to ADP ratio;
improvement in tolerance in immune defense and repair;
improvement of primary and secondary immune recycling of foreign invaders;

In another embodiment this disclosure provides a system comprising a magnesium complex comprising a magnesium citrate and a quaternary amine wherein the magnesium citrate is also known as magnesium 2-hydroxypropane-1,2,3-tricarboxylate. The quaternary amine comprises phosphatidylcholine and/or choline and wherein the magnesium complex includes at least one mono- di-, or tri-carboxylic acid. Wherein the system includes administering the magnesium complex nanodroplets formulated to improve blood pressure in hypertensive adults by administering at least one first dose of the magnesium complex, wherein the at least one first dose comprises 440 mg of elemental magnesium; and administering at least one second dose of the magnesium complex, wherein the at least one second dose comprises 440 mg of elemental magnesium.

In addition, the present disclosure includes a method comprising:
administering a magnesium complex comprising a magnesium citrate, a quaternary amine, and at least one carboxylic acid, and administering at least one first dose of the magnesium complex; and administering at least one second dose of the magnesium complex to study subjects.

This method includes a magnesium complex that comprises a dose of four soft-gels with a total concentration of 440 mg of elemental magnesium. This magnesium complex comprises 440 mg of element magnesium that is present as inverted micellar nanodroplets.

Here the method involves administering at least one first dose of magnesium complex and administering at least one second dose of magnesium complex occurs within approximately twenty-four hours.

The quaternary amine comprises phosphatidylcholine and/or choline.

This method involves magnesium, quaternary amine and at least one carboxylic acid such as citrate, malate, succinate, and/or mono-, di-, or tri-carboxylic acid or functionally identical counterions.

Here the complex can also be characterized as including a magnesium salt and acetylcholine as a quaternary amine.

As before the magnesium complex also comprises at least one or a combination of an acetate, glycinate, taurate, pidolate, bitartrate, bis-salicylate, succinate, fumarate, malate, citrate and/or ascorbate or other functionally equivalent counter ions.

In yet another embodiment the magnesium complex exits as nanodroplets that range in size between 0.1 micron and 100 microns that are bioavailable, bio-adsorbable, and bio-functional and wherein said nanodroplets can also exist as super nanodroplets that range in size of greater than 100 microns to a size of 300 microns that are bioavailable, bioabsorbable and bio-functional and wherein the complex forms multiple clusters of the nanodroplets as they are released into simulated digestive fluid that results in complete dispersion of the nanodroplets that yields a completely transparent simulated digestive fluid phase.

WORKING EXAMPLE

The working example provides one instance or more, specifically to describe formation of inverted stable micellar nanodroplets (that are primarily spherically shaped particles) which meet the necessary criteria for assuring the uptake of the magnesium complex. To acquire the proper delivery of the magnesium as neutral nanodroplets, a charge balance is a required. This requirement includes the need to not only neutralize the charge at the surface of the nanoparticle (nanodroplet) but also to neutralize the charge(s) of the ions within the nanoparticle to stabilize it.

In order to exemplify certain characteristics of the charged constituents to achieve a balanced charged inner portion of each nanosphere, there are 2 citrate ions that each have a –3 charge that equals a –6 overall charge. To balance or neutralize the negative charged citrate there exists 2 Mg ions, each with a +2 charge that equates to a +4 overall charge and 2 choline ions (each with a +1 charge that equates to a +2 overall charge). In this manner an overall stoichiometry is obtained that reflects balanced inner overall ionic charges that sum to zero. Equivalence is achieved when the charge distribution is stoichiometrically balanced.

By accomplishing the properly balanced stoichiometry the nanodroplet contains equal numbers of negative and positive charges inside a neutrally charged droplet that retains its integrity. This overall neutrality both within and on the surface of the nanodroplets, which are more accurately described as "inverted micellar nanodroplets" that refers to both the properly balanced stoichiometry with charged balanced counter ions within the nanodroplets and an outer shell portion (near and on the surface) of the nanodroplets also being neutrally charged. This overall neutrality (both within and on the surface of the nanodroplets) provides the necessary bioavailability required to achieve the efficacy to meet the demands of alleviating and/or eliminating the magnesium deficit conditions described herein.

For example, it is also observed that these nanodroplets are provided in a size distribution of up to 100 microns which allows for complete miscibility within simulated intestinal fluid used. Above 100 microns and to at least 300 microns the nanodroplets become "super nanodroplets" that remain bioavailable. More specifically, when the contents of the nanodroplets are in proper proportions and observed within the simulated intestinal fluid vial the nanodroplets remain nanodroplets as they are dispersed in a diaphanous manner becoming transparent.

If the proper charges, sizes, and sequences of the nanodroplets are maintained there will be complete release of the contents of the soft-gel that houses the elemental magnesium for proper delivery. If not, then the droplets can either coalesce at the top portion of the simulated intestinal fluid or a gelation can occur which leads to a bottom portion phase separation. The goal is to prevent coacervation and/or agglomeration of these nanodroplets so that neither the top portion or bottom portion indicates coacervation or separation.

Clinical data supports the hypothesis that these nanodroplets are neutral on the surface and charged on the interior while remaining relatively small (typically up to 100 microns) in the aggregate. This allows for both bioactive and bioavailable Mg ions to disperse into the bioavailable pool of total body magnesium which is about 20% of the total body magnesium.

The method regarding how nanodroplets disperse in simulated intestinal fluid over time can be described as follows. A timeline exists for release of the soft-gel contents into simulated intestinal fluid. What we want to convey is that the release of the contents of the soft-gel occurred slowly and dispersed completely into the fluid so that the dispersion of the soft-gel contents results in a clear or transparent solution. This is the desired end-result.

If an oily top layer forms it indicates that the nanodroplets have coalesced and lost their ability to be taken up by the body. The basket containing the soft-gels was immersed in simulated intestinal fluid at 37° C. and stirred at 700 RPM to maintain constant temperature. When the release of the soft-gel contents occurs, there are only three possibilities. The nanodroplets might disperse completely into the fluid. The contents of the soft-gel might float to the top of the vessel indicating that they were no longer nanodroplets. The contents might have become a coacervate which also cannot be taken up by mammals. Fortunately, the results of the study reported here support the nanodroplet characteristics of the contents of the soft-gel.

It would be unduly repetitious and obfuscating to describe and illustrate every combination and sub-combination of these embodiments. The claims as presented represent some of these different embodiments but are not intended to be fully encompassing of every aspect of the present disclosure and accompanying invention.

I claim:

1. A method of treatment to reduce blood pressure in a hypertensive adult within 7 days comprising; administering a magnesium complex to the hypertensive adult, wherein said complex is magnesium 2-hydroxypropane-1,2,3-tricarboxylate and a quaternary amine and wherein said magnesium complex provides nanodroplets that are neutrally charged on an exterior surface of said nanodroplets and wherein within said nanodroplets there are equal negative and positive charges that stabilize said nanodroplets to provide inverted micellular nanodroplets and wherein said inverted micellular nanodroplets are disposed within tablets and/or soft gels, wherein said hypertensive adult is administered at least one first dose of said magnesium complex, wherein said at least one first dose comprises 440 mg of elemental magnesium and at least one second dose of said magnesium complex, wherein said at least one second dose comprises 440 mg of elemental magnesium so that at an end of said treatment, the seated median blood pressure is decreased in the hypertensive adult.

2. The method of claim 1, wherein, after said treatment, the seated median blood pressure of the hypertensive adult is reduced by 5.7 mmHg.

* * * * *